United States Patent [19]

Ling et al.

[11] Patent Number: 4,740,587

[45] Date of Patent: Apr. 26, 1988

[54] INHIBIN AND METHOD OF PURIFYING SAME

[75] Inventors: Nicholas C. Ling; Shao-Yao Ying, both of San Diego; Fred S. Esch, Oceanside; Roger C. L. Guillemin, La Jolla, all of Calif.

[73] Assignee: The Salk Institute for Biological Studies, San Diego, Calif.

[21] Appl. No.: 784,436

[22] Filed: Oct. 3, 1985

Related U.S. Application Data

[63] Continuation-in-part of Ser. No. 756,866, Jul. 18, 1985, abandoned.

[51] Int. Cl.$^4$ .................. A61K 37/02; C12P 21/02
[52] U.S. Cl. ...................... 530/313; 530/324; 530/325; 530/326; 530/327; 530/328; 530/344; 530/350; 435/70
[58] Field of Search ............ 530/313, 324, 325, 326, 530/327, 328, 344, 350; 435/70

[56] References Cited

PUBLICATIONS

Miyamoto et al., *Biochemical and Biophysical Research Communications*, vol. 129, No. 2, pp. 396–403.

*Primary Examiner*—Delbert R. Phillips
*Assistant Examiner*—Nathan M. Nutter
*Attorney, Agent, or Firm*—Fitch, Even, Tabin & Flannery

[57] ABSTRACT

Two 32,000-dalton proteins with inhibin activity were isolated from porcine follicular fluid using heparin-Sepharose affinity chromatography, followed by gel filtration on Sephacryl S-200 and then four steps of reverse-phase high-performance liquid chromatography. Each isolated molecule is composed of two chains having molecular weights of about 18,000 and about 14,000 daltons, respectively, which are bound together by disulfide bonding. Microsequencing revealed the NH$_2$-terminal portion of the 18K chain of both to be Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val, of one of the 14K chains to be Gly-Leu-Glu-Cys-Asp-Gly-Arg-Thr-Asn-Leu-Cys-Cys-Arg-Gln-Gln-Phe-Phe-Ile-Asp-Phe-Arg-Leu-Ile-Gly-Trp, and of the other 14K chain to be Gly-Leu-Glu-Cys-Asp-Gly-Lys-Val-Asn-Ile-Cys-Cys-Lys-Lys-Gln-Phe-Phe-Val-Ser-Phe-Lys-Asp-Ile-Gly-Trp-Asn-Asp-Trp-Ile-Ile-Ala-Pro. Both proteins have now been completely characterized, each having a first chain 134 residues long linked by disulfide bonding to a second chain 116 or 115 residues long. The first chain is believed to be glycosylated, which accounts for the disparity between the number of residues and the apparent molecular weight of 18K. These 32K proteins specifically inhibit basal secretion of FSH, but not of LH, in a rat anterior pituitary monolayer culture system. The half-maximal effective does of one is 450 pg/ml and of the other is 900 pg/ml.

20 Claims, 7 Drawing Sheets

INHIBIN AND METHOD OF PURIFYING SAME

This invention was made with Government support under Grant Nos. HD-09690 and AM-18881, awarded by the National Institute of Health. The Government has certain rights in this invention.

This application is a continuation-in-part of our earlier application Ser. No. 756,866, filed July 18, 1985 now abandoned.

The present invention relates to a protein having inhibin activity isolated substantially to homogeneity from bodily material obtained from porcine animals. The invention also relates to a method of purifying porcine inhibin.

BACKGROUND OF THE INVENTION

The concept of inhibin as a water-soluble substance produced in the gonad but acting specifically at the pituitary level to inhibit the secretion of follicle-stimulating hormone (FSH) was postulated by McCullagh in 1932 (*Science*, 76, 19-20). Such preferential regulation of the gonadotropin secretion has generated a great deal of interest and has prompted many laboratories in the past fifty years to attempt to isolate and characterize this substance from extracts of testis, spermatozoa, rete testis fluid, seminal plasma and ovarian follicular fluid, using various bioassays. Although many reports have appeared in the literature claiming the purification of inhibin-like material with molecular weights ranging from 5,000 to 100,000 daltons, subsequent studies have shown that these substances were either not homogenous or did not have the high specific activity expected of true inhibin (de Jong, *Molecular & Cellular Endocrin.*, 13, 1-10 (1979)). Materials having inhibin activity may be used to regulate fertility in mammalian animals, particularly male animals.

SUMMARY OF THE INVENTION

In accordance with the present invention, two proteins both having a molecular weight of about 32,000 daltons and having inhibin activity have been successfully isolated from porcine follicular fluid. These two proteins have been completely characterized using microsequencing and molecular biological methods.

The proteins were isolated to substantial homogeneity from material obtained from the bodies of porcine animals and are hereinafter referred to as Protein A and Protein B. Each protein has a molecular weight of about 32,000 daltons (32K) and is composed of two polypeptide chains having molecular weights of 18,000 and 14,000 daltons, respectively, the chains being linked together in the biologically active protein by disulfide bonding. Microsequencing showed that the amino-terminal amino acid residue sequence of the 18,000 dalton (18K) chain of both proteins was Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val and that the first six residues of both amino-terminals of the 14,000 dalton (14K) chains were the same, namely Gly-Leu-Glu-Cys-Asp-Gly. It was also ascertained that the first ten residues of the 14K chain of Protein B were Gly-Leu-Glu-Cys-Asp-Gly-Arg-Thr-Asn-Leu. Proteins A and B have now been completely characterized as a result of further microsequencing and the use of molecular biological techniques. Each 32K protein exhibits inhibin activity in that it specifically inhibits basal secretion of FSH but does not inhibit basal secretion of luteinizing hormone (LH). The individual chains are not biologically active.

Purification of porcine inhibin to substantial homogeneity, i.e., about 90% by weight of total protein in the fraction, was achieved through a combination of protein separation procedures including heparin-Sepharose affinity chromatography, gel filtration and reverse-phase, high-performance liquid chromatography (RP-HPLC).

(a) Heparin-Sepharose affinity chromatography of PFF. The inhibin protein was eluted with 1M NaCl in 0.01M Tris-HCl, pH 7.

(b) Sephacryl S-200 gel filtration of the PFF inhibin proteins. The effluent fractions indicated by the solid bar near the bottom of FIG. 1a were pooled, dialyzed and then divided into eight equal portions for this gel filtration. The profile from one of the columns is indicative of each column and is shown.

(c) RP-HPLC purification of the inhibin proteins recovered from gel filtration. The components of the active region from the gel filtration, as determined by in vitro bioassay and designated by the solid bar in FIG. 1b, were pooled, lyophilized and, after dissolving in 0.2 N acetic acid, applied directly onto a Vydac C4 column and eluted with the indicated gradient of acetonitrile in the TEAP buffer system at 9 ml/3 min. Two inhibin proteins, Proteins A and B, indicated by the solid bars in FIG. 1c, were recovered.

Figure 1A:
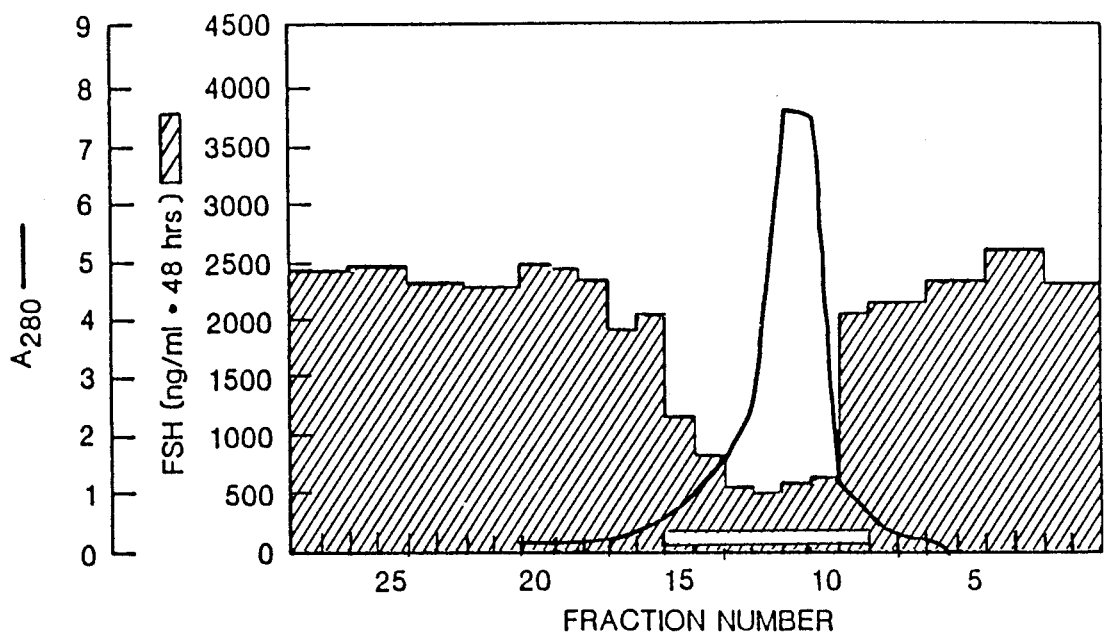
FIG. 1 shows chromatograms representing initial steps of purifications of inhibin proteins from porcine follicular fluid (PFF) under conditions described as follows.
Figure 1B:
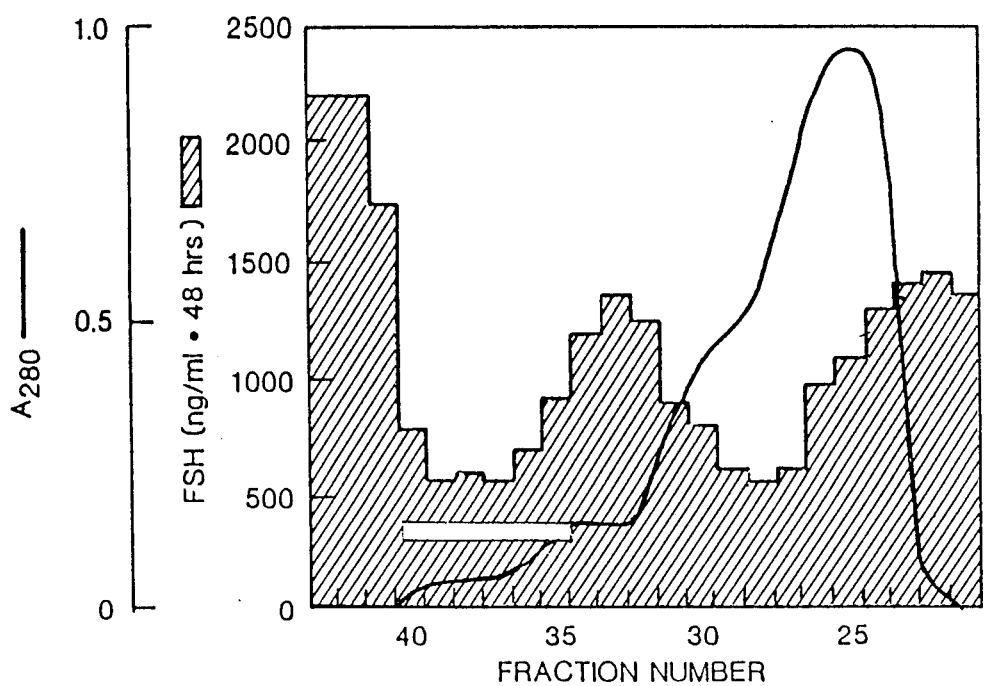
Figure 1C:
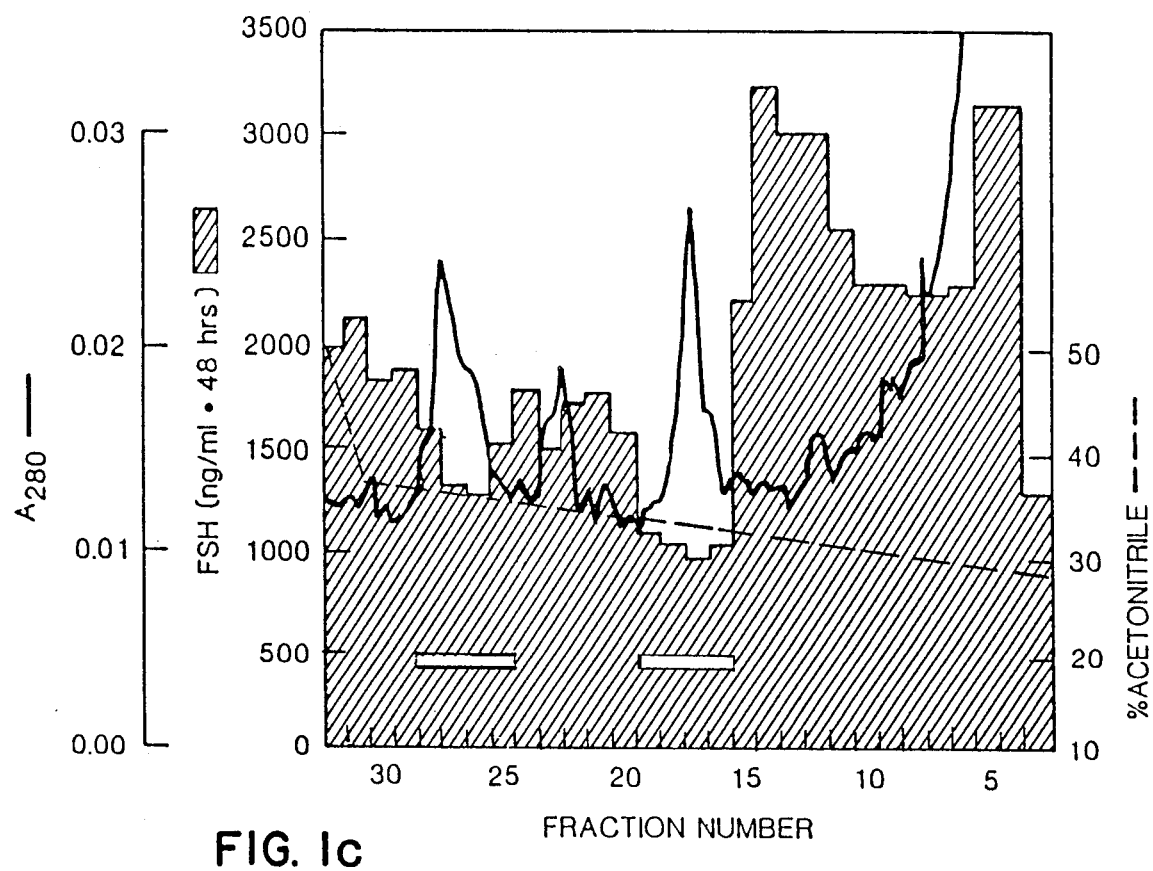

FIG. 2 shows chromatograms of RP-HPLC purification of inhibin Protein B as follows:

(a) The active fractions designated by the solid bar under B in FIG. 1c were pooled and, after being diluted to 3 times their original volume, applied directly onto a Vydac C4 column and eluted with the indicated gradient of acetonitrile in trifluoroacetic acid (TFA) buffer system at 9 ml/3 min.

Figure 2A:
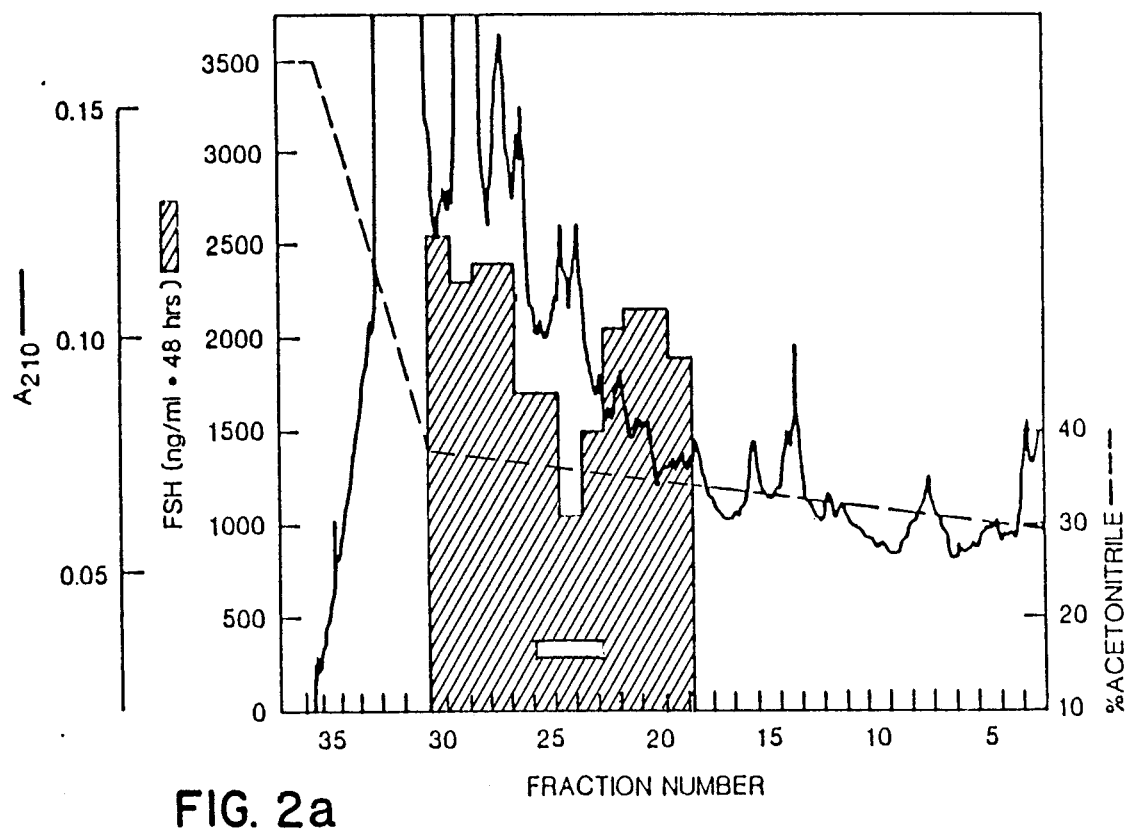

(b) The active material denoted by the solid bar in FIG. 2a was pooled, diluted to 3 times its original volume and likewise purified on a Vydac Phenyl column with the indicated gradient of acetonitrile in triethylammonium phosphate (TEAP) buffer system at 2 ml/2 min.

Figure 2B:
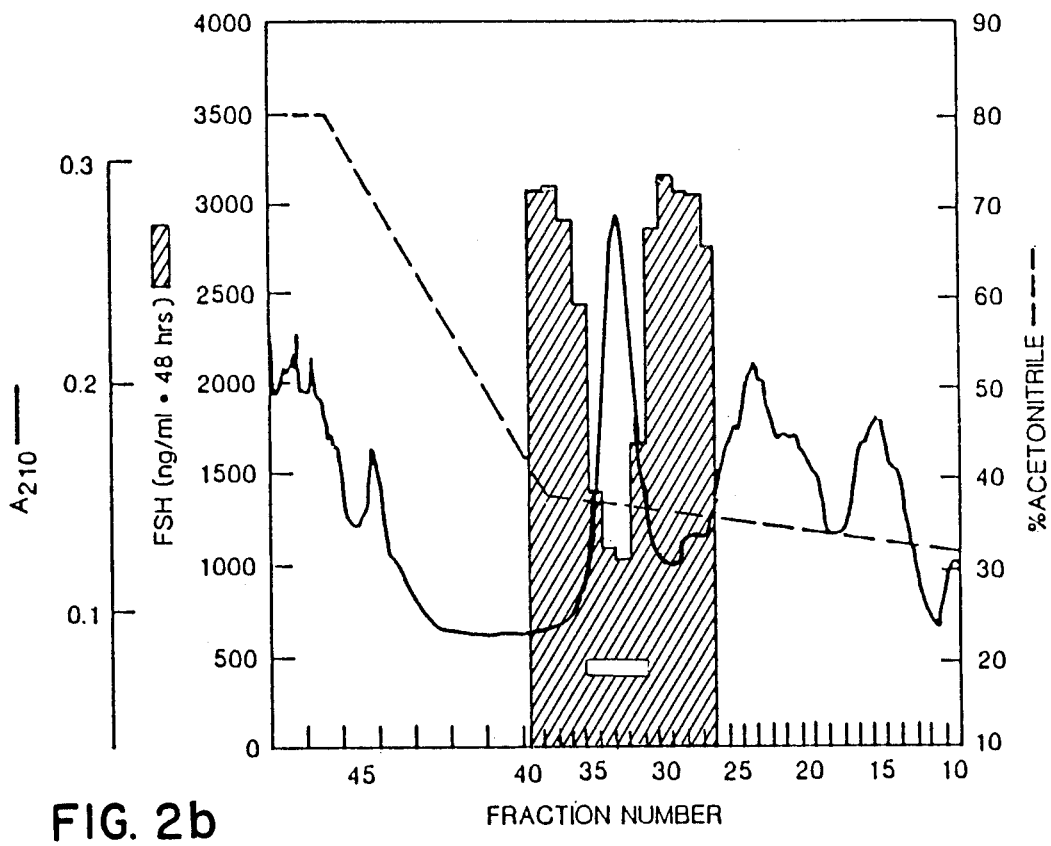

(c) The active material accumulated from a number of columns identical to that represented by the chromatogram of FIG. 2b was pooled and concentrated on an Aquapore RP-300 column with the indicated gradient of acetonitrile in the TFA buffer system at 0.5 ml/min.

Figures 3A, 3B:
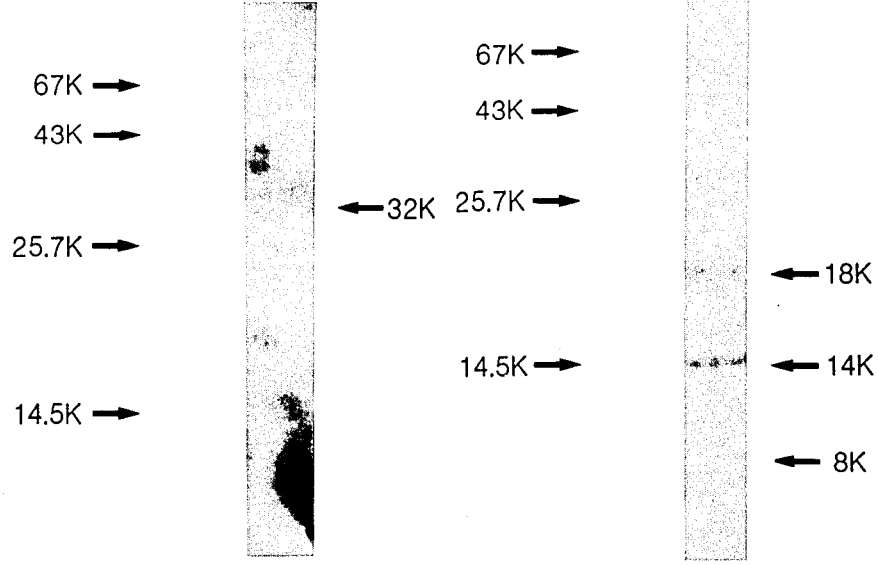

FIG. 3 shows actual electrophoretic results of sodium dodecylsulfate-polyacrylamide gel electrophoresis (SDS-PAGE) analysis of the purified inhibin Protein B as follows:

(a) Analysis of Protein B under non-reducing condition.

(b) Analysis of Protein B under reducing condition. The molecular weight standards are indicated on the left.

Figure 4:
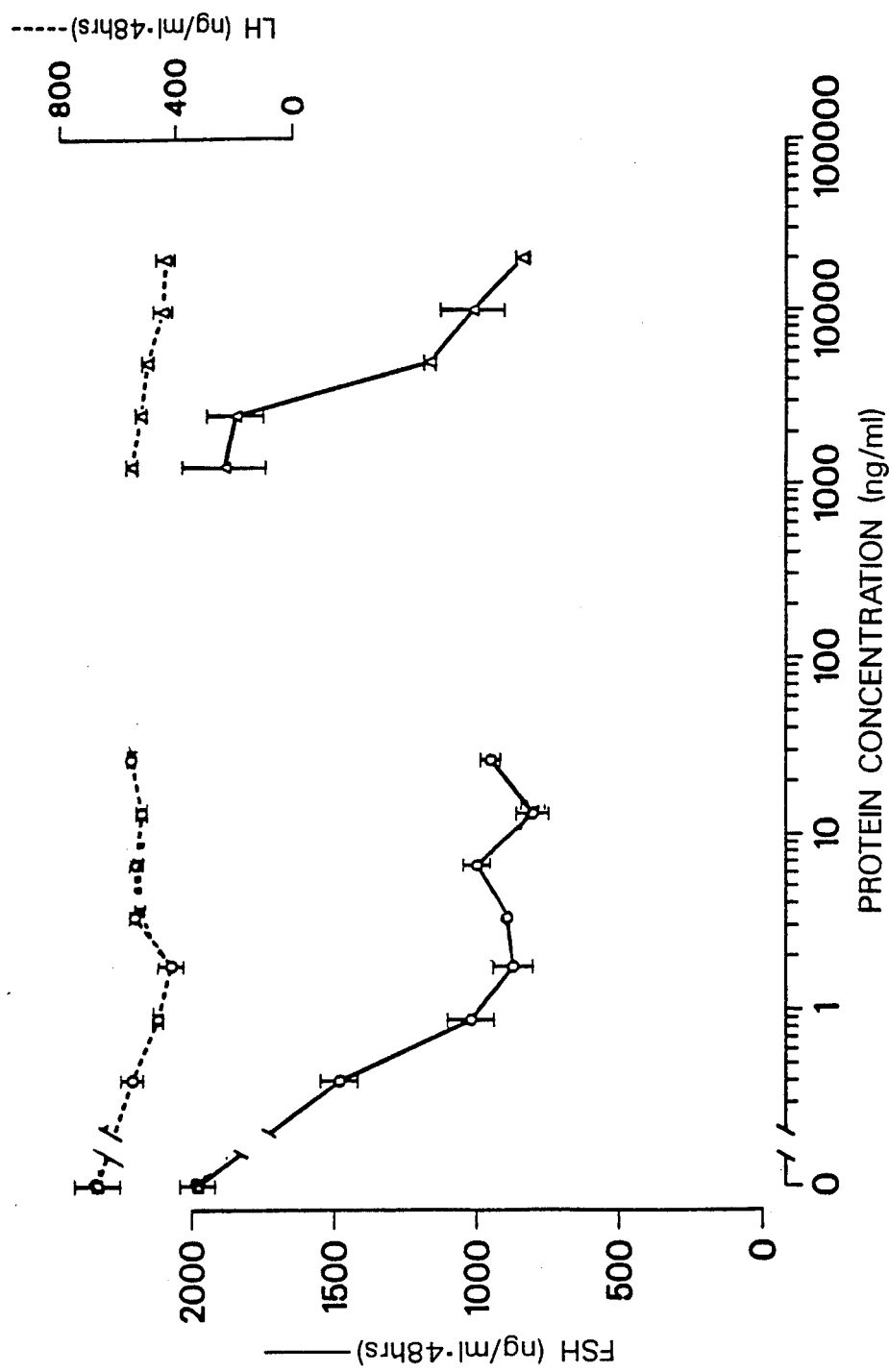

FIG. 4 shows dose-response curves of the purified inhibin Protein B (O), as well as the crude PFF standard (Δ) on the basal secretion of FSH and LH from rat anterior pituitary cell cultures. The crude PFF standard was a charcoal-stripped and 40% saturated ammonium sulfate precipitate of PFF, Schwartz, N. et al. *Proc Natl. Acad. Sci. USA* 74 5721–5724 (1977).

FIG. 5 shows chromatograms of RP-HPLC purification of inhibin Protein A as follows:

(a) The active fractions designated by the solid bar under A in FIG. 1c were pooled and, after being diluted to 3 times their original volume, applied directly onto a Vydac C4 column and eluted with the indicated gradient of acetonitrile in trifluoroacetic acid (TFA) buffer system at 9 ml/3 min.

Figure 5A:
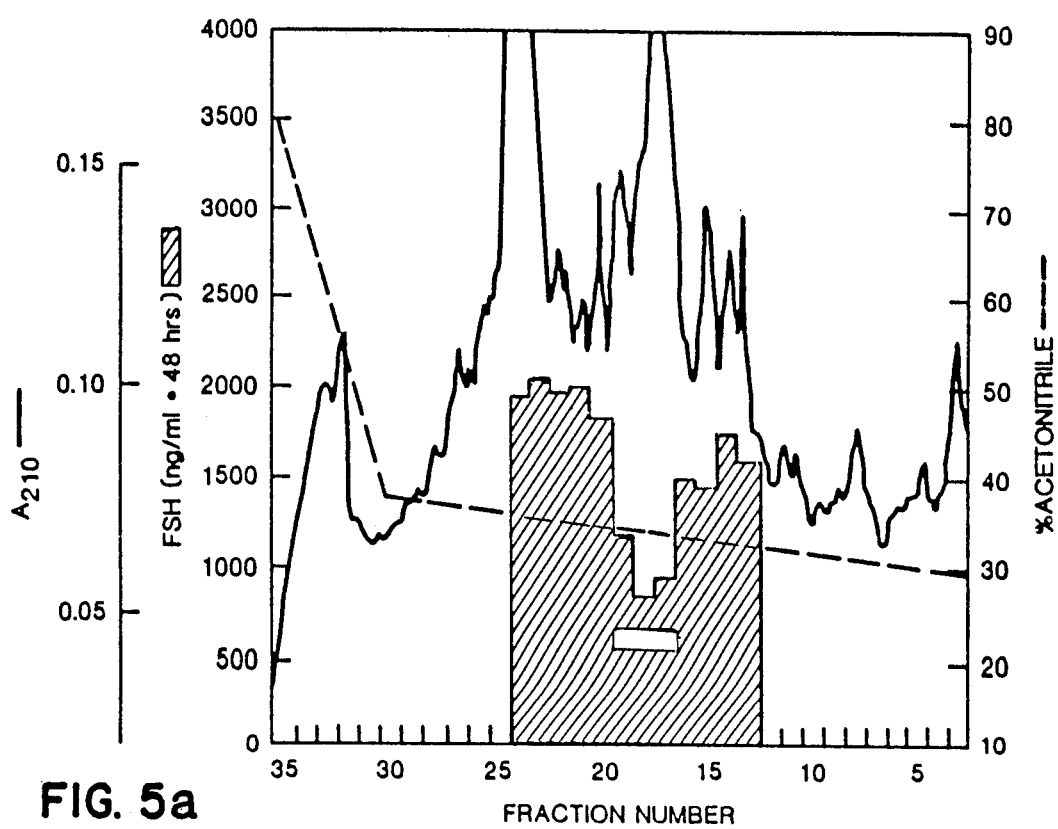

(b) The active material denoted by the solid bar in FIG. 5a was pooled, diluted to 3 times its original volume and likewise purified on a Vydac Phenyl column with the indicated gradient of acetonitrile in triethylammonium phosphate (TEAP) buffer system at 2 ml/2 min.

Figure 5B:
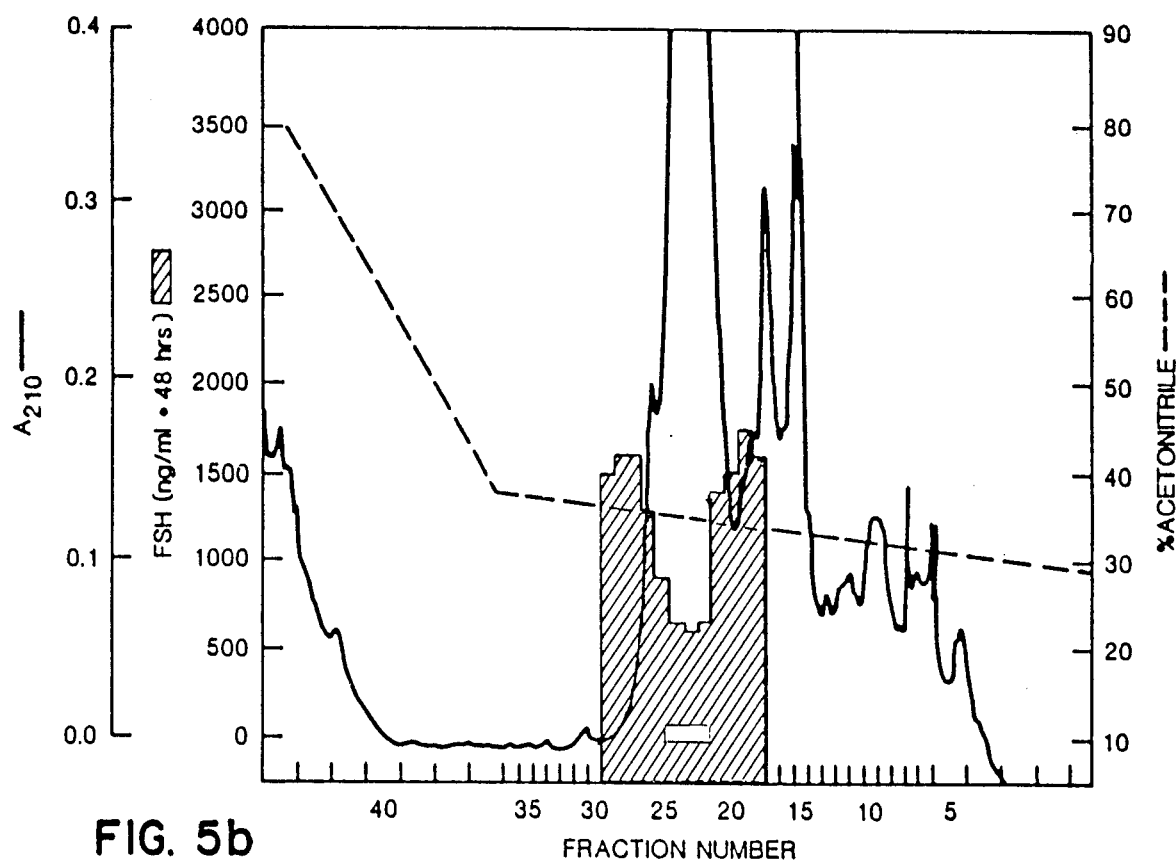

(c) The active material accumulated from a number of columns identical to that represented by the chromatogram of FIG. 5b was pooled and concentrated on an Aquapore RP-300 column with the indicated gradient of acetonitrile in the TFA buffer system at 0.5 ml/min.

DETAILED DESCRIPTION OF THE PREFERRED EMBODIMENTS

Using a multi-step procedure, two 32,000 dalton peptides were isolated to substantial homogeneity from porcine follicular fluid (PFF). Each protein (Protein A and Protein B) is composed of two chains of 18K and 14K, respectively, and the chains of the intact molecule are held together by disulfide bonding, the linkage between the chains being necessary for biological activity. An amino acid analysis of the total protein has been performed for each, and the amino acid residue sequence of the amino-terminus of each chain has been determined by microsequencing. The amino-terminal sequence of the 18K chain of each protein was found to be: Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val. As a result of further work, it is believed that both 18K chains have exactly the same sequence of 134 amino acid residues and have a free acid C-terminus.

Microsequencing initially showed that the amino-terminal sequences of the 14K chains of the first six residues of both chains were the same and that the first ten residues of the 14K chain of Protein B were Gly-Leu-Glu-Cys-Asp-Gly-Arg-Thr-Asn-Leu. Further sequencing showed that the next 15 residues were $X_{11}$-$X_{12}$-Arg-Gln-Gln-Phe-Phe-Ile-Asp-Phe-Arg-Leu-$X_{23}$-Gly-Trp, with $X_{11}$ possibly being Ser, with $X_{12}$ likely being Cys and with $X_{23}$ being Ile or Leu. Later it was determined that both $X_{11}$ and $X_{12}$ were Cys and that $X_{23}$ was Ile. The ability to sequence the chains demonstrates that the protein has been purified to at least about 90% by weight of total protein as do the sharp elution peaks of the protein in the final chromatographic purification step.

The C-termini of all three chains are free acid. Further microsequencing showed that the N-terminus of the 14K chain of Protein A has the following sequence: Gly-Leu-Glu-Cys-Asp-Gly-Lys-Val-Asn-Ile-Cys-Cys-Lys-Lys-Gln-Phe-Phe-Val-Ser-Phe-Lys-Asp-Ile-Gly-Trp-Asn-Asp-Trp-Ile-Ile-Ala-Pro.

Protein A has now been completely characterized and found to include a 134-residue chain (the 18K chain) that is linked by one or more disulfide bridges to a 116-residue chain (the 14K chain) which appears to include at least one internal disulfide bridge. Protein B has the same 18K chain linked to a homologous 14K chain.

Each 32K protein is acidic, having a pKa of 4.8, and is generally soluble in aqueous media. Each is glycosylated to a limited extent, as determined by limited affinity to concanavalin A. Each 32K protein exhibits inhibin activity in that it specifically inhibits basal secretion of FSH in a rat anterior pituitary monolayer culture system. Protein B exhibits a half-maximal effective dose of 450 pg/ml, as calculated by the computer program BIOPROG, and Protein A exhibits an $ED_{50}$ of 900 pg/ml. Each 32K protein is useful for regulating fertility of mammalian animals, particularly males.

Each 32K protein has apparent similarities to a 56,000 dalton (56K) protein isolated from bovine follicular fluid, a protein composed of two chains of molecular weights 44,000 and 14,000 daltons (44K and 14K) bound together by disulfide bonds. The first three amino-terminal residues of the 44K bovine chain reported by Robertson et al., *Bio. Chem. Biophys. Res. Commun.* 176 220–226 (1985) are different from either of the two chains of either of the 32K porcine proteins that were isolated, but the second and third residues of the 14K chain of the 56K bovine peptide are identical to those of the 14K chain of both of the 32K porcine peptides. The full relationship, if any, between the 32K porcine proteins and the 56K bovine protein is not known at this time.

Each 32K protein is definitely different from the "alpha-inhibins" Ramasharma, K. et al. *Science* 223, 1199–1201 (1984); Li, C. H. et al., *Proc. Natl. Acad. Sci. USA* 82 4041–4044 (1985) and "beta-inhibin" Seidah, N. *FEBS Letter* 175 349–354 (1985) recently isolated and characterized from human seminal plasma. "Alpha-inhibins" are reported to be single-chain polypeptides all derived from a 92-amino-acid-residue parent molecule. However, neither a synthetic replicate of the 31-amino-acid $NH_2$-terminal fragment of alpha-inhibin-52 nor the native product inhibited the basal FSH-releasing activity in the rat anterior pituitary cell culture, Yamashiro, D. et al., *Proc. Natl. Acad. Sci. USA* 81 5349–5402 (1984). "Beta-Inhibin" is described as a single-chain polypeptide with 94 amino acid residues, with the bioactive core allegedly residing at the COOH-terminal 67–94 fragment, Arbatti, N. et al. *FEBS Letters*, 181, 57–63 (1985). This fragment has been synthesized, but it is found to be inactive, up to a concentration of 5 μg/ml, to inhibit the basal secretion of FSH in the rat anterior pituitary cell culture assay. The bioassay methods (for "inhibin activity") used in these two laboratories, Ramasharma et al. supra. and Li et al. supra., are substantially different from those described herein.

In an inhibin purification procedure according to the invention, porcine inhibin is isolated from crude extract material obtained from a porcine animal body, specifically porcine follicular fluid (PFF) although other appropriate bodily extracts might be used, by successive purification procedures that include heparin-Sepharose affinity chromatography, gel filtration and at least one and preferably several RP-HPLCs of different conditions of stationary phase and/or mobile phase. The same procedure is useful in obtaining a desired mammalian inhibin protein from a crude extract resulting from recombinant DNA processes.

In the preferred procedure by which porcine inhibin was first isolated to substantial purity, PFF was first purified by heparin-Sepharose affinity chromatography, next by gel filtration on Sephacryl S-200 gel and then with four successive RP-HPLCs using different mobile phase gradients and/or derivatized silica supports. Preferably stationary phases having relatively low hydrophobicity are used, with C3–C8 columns being preferred and C3–C5 and phenyl columns being particularly preferred. Solute specificity of the mobile phase is preferably adjusted by varying the concentration of an organic component, particularly acetonitrile. Although a single RP-HPLC fractionation significantly increases the purity relative to the gel-filtrated material, two or more, and preferably four, RP-HPLC purifications are generally performed subsequent to successive treatment by heparin-Sepharose chromatography and gel filtration.

The starting material for the procedure was frozen PFF that was procured from J. R. Scientific, Woodland, Calif. Approximately 18 liters of such frozen PFF were processed in 250 ml batches to isolate the inhibin product. The first step of the purification was heparin-Sepharose affinity chromatography, in which the protein is adsorbed to the Sepharose-bound heparin moieties under application conditions, and the adsorbed inhibin material is recovered by 1M NaCl elution. This step greatly expedites the purification procedure for crude extracts because it allows a relatively large volume of a crude extract, such as PFF, to be processed fairly rapidly while recovering an amount of protein exhibiting total inhibin activity equal to at least 90% of that of the curde extract.

Throughout the purification procedure, the inhibin bioactivity was monitored by an in vitro bioassay using rat anterior pituitary monolayer culture, Vale, W. et al. *Endocrinology*, 91, 562–572 (1972). In brief, 21-day-old female rat anterior pituitaries are collected, enzymatically dispersed and plated in 10% fetal bovine serum in HDMEM (GIBCO Laboratories, Santa Clara, Calif.) into 24-well tissue culture plates (Falcon Plastic, Oxnard, Calif.) on day 1. On day 2, the medium is changed to 1% fetal bovine serum in HDMEM, and the sample is added. Incubation is continued for another 48 hours. The medium is then harvested, and the LH and FSH contents are determined by radio-immunoassay (RIA) using materials provided by The Pituitary Hormone Program of NIADDKD. In this assay, the inhibin proteins inhibit the basal release of FSH only but not that of LH, as compared to control cells that receive the incubation medium only.

For the detection of inhibin activity in the various column fractions, aliquots ranging from 0.01% to 0.1% by volume were removed, and after adding 100 $\mu$g human serum albumin in 100 $\mu$l water, the solvents were evaporated in a Speed-Vac concentrator (Savant, Hicksville, N.Y.). The residue was redissolved in 3 ml 1% fetal bovine serum in HDMEM, filtered through a Millex-GS 0.22 $\mu$m filter (Millipore Corp., Bedford, Mass.) and assayed in duplicate. To speed up the bioassays during the purification process, only basal inhibition of FSH secretion exerted by the inhibin activity was determined and plotted in the region where the inhibin proteins were expected to migrate in the chromatograms.

To perform the heparin-Sepharose affinity chromatography, a 500 ml bottle of frozen PFF was defrosted, and the cell debris were spun down in a Beckman J2-21 centrifuge (Beckman Instruments, Inc., Palo Alto, Calif.) using a JA-20 rotor at 10,000 rpm for 30 minutes. One half of the supernatant (250 ml) was diluted to 10 times its volume by the addition of 2,250 ml of 0.01 M Tris-HCl containing 0.1 M NaCl, pH 7, in a 4 liter Erlenmeyer flask and pumped simultaneously via eight silastic tubes (0.76 mm ID) into eight heparin-Sepharose (Pharmacia Fine Chemicals, Piscataway, N.J.) columns (3.5×9 cm) by two Rabbit 4-channel peristaltic pumps (Rainin Instrument Co., Inc., Emeryville, Calif.) at 40 ml/hr per column. After all the fluid had been pumped through the heparin-Sepharose, the eight columns were washed simultaneously with 3.5 liters of 0.01 M Tris-HCl, pH 7, containing 0.1M NaCl in the same manner. The adsorbed proteins with inhibin activity were removed by washing the eight columns simultaneously with 1.3 liters of 0.01M Tris-HCl containing 1M NaCl, pH 7, as above, and the wash was collected into fractions of 16 ml. FIG. 1a shows a typical elution profile of the inhibin activity material from PFF. The inhibin activity was monitored by the in vitro bioassay described above. The columns were regenerated by further washing with 1.6 liters 2M NaCl in 0.01M Tris-HCl, pH 7, and re-equilibrated with 3.5 liters 0.01M Tris-HCl containing 0.1M NaCl for purification of the remaining 250 ml of PFF.

Next, the material was fractionated by gel filtration to separate proteins generally according to their molecular weights. The fractions having inhibin activity extracted by the eight heparin-Sepharose columns were pooled (400 ml) and dialyzed overnight to remove NaCl in a 28.6 mm cylinder diameter Spectrapor No. 3 membrane tubing with $M_r$ cutoff at 3,500 (Spectrum Medical Industries, Inc., Los Angeles, Calif.) against 16 liters of 30% acetic acid. The retained fluid was centrifuged, as above, to remove a white precipitate, and the supernatant was divided into eight equal portions for applying to eight 5×100 cm Sephacryl S-200 superfine columns (Pharmacia Fine Chemicals, Piscataway, N.J.). Each column was eluted with 30% acetic acid at 20 ml for 22 min., and the column fractions were monitored by UV absorption at 280 nm and by bioassay.

FIG. 1b shows the elution profile of the inhibin material purified in a Sephacryl S-200 column. Two elution zones of approximately equal amounts of activity were detected, one eluting at $M_r$ about 30,000 and the other at $M_r$ about 12,000. However, based upon the protein concentration a determined by UV absorption, the low-molecular-weight zone contains much higher specific activity. As a result, this region was selected for further purification by RP-HPLC.

The low-molecular-weight inhibin protein from the eight S-200 columns was pooled and lyophilized. The lyophilized material (40 mg) was dissolved in 40 ml 0.2N acetic acid and filtered through a Millex-HA 0.45 $\mu$m filter (Millipore Corp., Bedford, Mass.). The filtrate was applied directly onto a 1×25 cm Vydac 5-$\mu$m particle-size C4 column (The Separations Group, Hesperia, Calif.) and developed with a gradient of TEAP buffer as shown in FIG. 1c. In the TEAP system, buffer A consists of 0.25 N. triethylammonium phosphate, pH 3, and buffer B is 80% acetonitrile in buffer A. After all the filtrate had been loaded, the column was washed with the aqueous buffer A until the UV absorption reached baseline. The fractions exhibiting inhibin activity were separated in a Beckman 332 gradient liquid chromatography system (Beckman Instruments, Inc., Berkely, Calif.) equipped with a Spectroflow 757 UV detector (Kratos Analytical Instruments, Ramsey, N.J.), a Soltec 220 recorder (Soltec Corp., Sun Valley, Calif.) and a Redirac 2112 fraction collector (LKB Instruments, Inc., Gathersburg, Md.). Two zones of substantial inhibin activity were detected, with more activity exhibited by the earlier eluting zone (inhibin Protein A) than the later eluting zone (inhibin Protein B), see FIG. 1c.

Inhibin Protein B from the various columns were pooled and further purified by two more RP-HPLC steps.

Figure 2C:
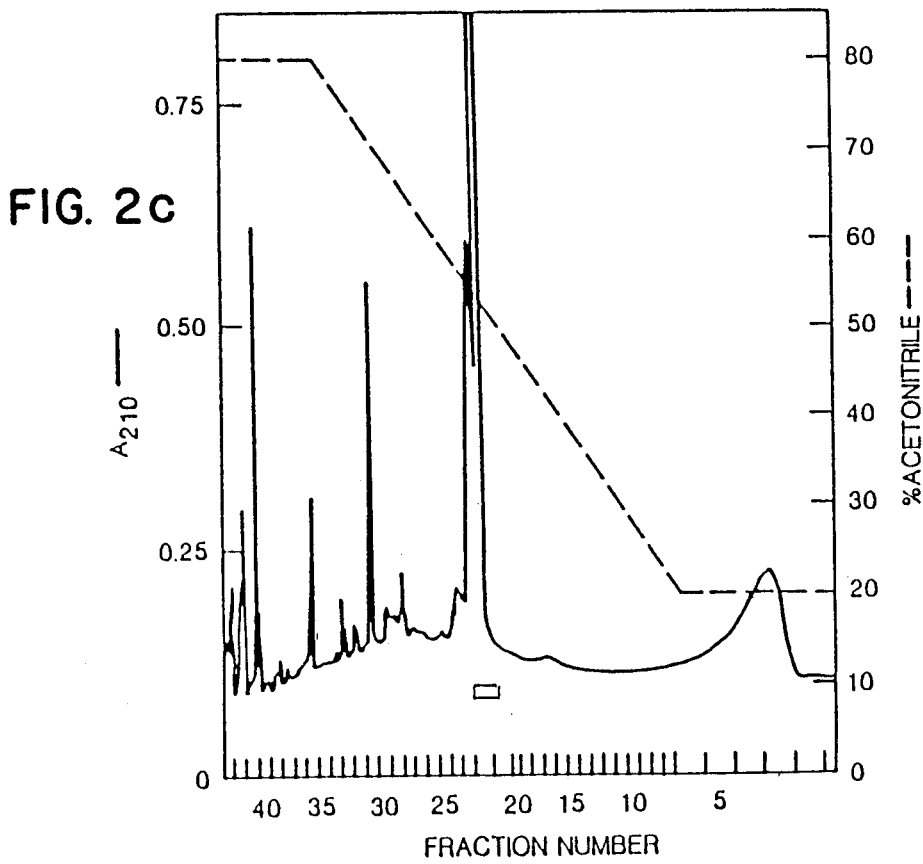

The first step uses a 1×25 cm Vydac 5-μm-particle-size C4 column and a trifluoroacetic acid (TFA) buffer system (FIGS. 2a) and the second step employs a 1×25 cm Vydac 5-μm-particle-size Phenyl column and the TEAP buffer system, as shown in FIG. 2b. In the TFA system, buffer A contains 1 ml trifluoracetic acid in 999 ml water and buffer B is 1 ml trifluoroacetic acid in 199 ml water and 800 ml acetonitrile. Finally, inhibin Protein B accumulated from a few batches was concentrated by RP-HPLC using a 0.46×25 cm Aquapore RP-300 10 μm-particle-size column (Brownlee Labs., Santa Clara, Calif.) and the TFA buffer system as shown in FIG. 2c. Altogether, a total of approximately 60 μg of inhibin Protein B was purified from the 18 liters of PFF.

Figure 5C:
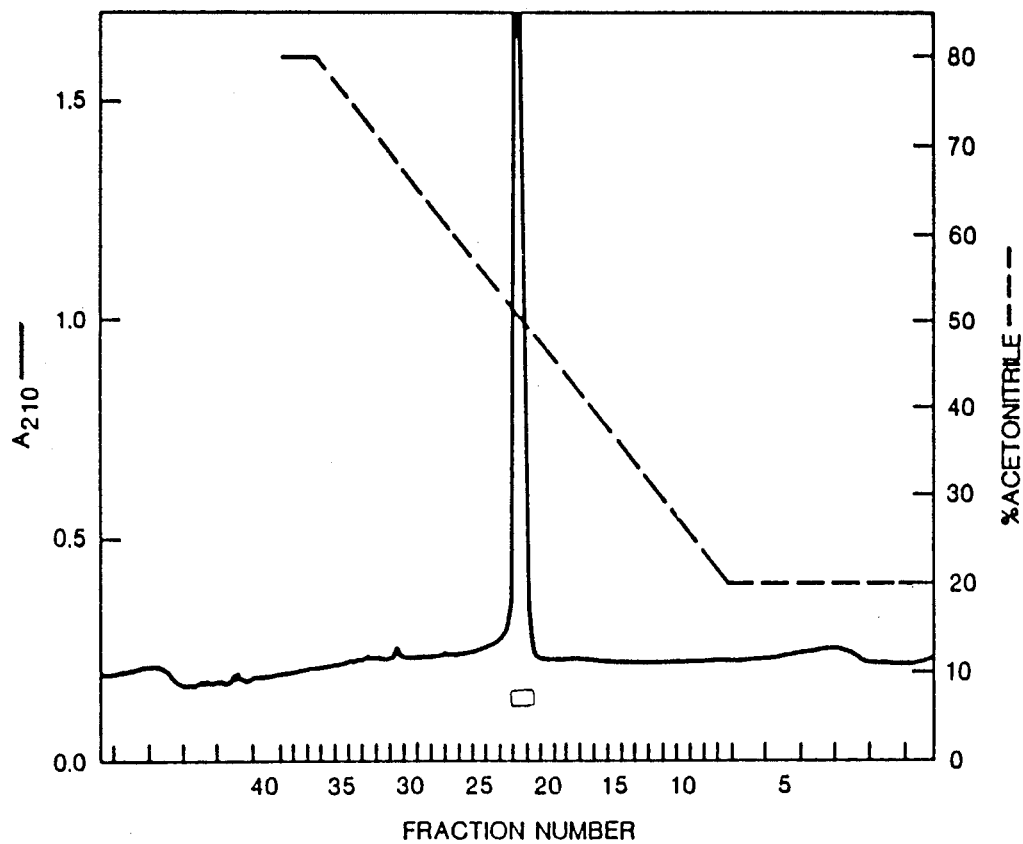

Inhibin Protein A from the various columns was pooled and further purified by two more RP-HPLC steps. The first step uses a 1×25 cm Vydac 5-μm-particle-size C4 column and a trifluoroacetic acid (TFA) buffer system (FIGS. 5a) and the second step employs a 1×25 cm Vydac 5-μm-particle-size Phenyl column and the TEAP buffer system, as shown in FIG. 5b. In the TFA system, buffer A contains 1 ml trifluoroacetic acid in 999 ml water and buffer B is 1 ml trifluoroacetic acid in 199 ml water and 800 ml acetonitrile. Finally, inhibin Protein A accumulated from a few batches were concentrated by RP-HPLC using a 0.46×25 cm Aquapore RP-300 10 μm-particle-size column (Brownlee Labs., Santa Clara, Calif.) and the TFA buffer system as shown in FIG. 5c. Altogether, a total of approximately 600 μg of inhibin Protein A was purified from the 18 liters of PFF.

Amino acid analyses of the substantially homogeneous inhibin Proteins A and B were performed as described in Bohlen P., et al. *Anal. Biochem.* 126 144–156 (1982), and the results are shown in Table 1 below.

TABLE 1

| AMINO ACID COMPOSITION OF PURIFIED INHIBIN PROTEIN FROM PORCINE FOLLICULAR FLUID | | |
|---|---|---|
| Amino Acid | Protein A* | Protein B* |
| Asx | 18.5 ± 1.6 | 21.0 ± 1.1 |
| Thr | 11.5 ± 0.5 | 13.5 ± 0.6 |
| Ser | 16.3 ± 1.4 | 18.1 ± 0.7 |
| Glx | 21.3 ± 1.4 | 22.5 ± 0.5 |
| Gly | 19.9 ± 1.9 | 22.4 ± 0.7 |
| Ala | 19.7 ± 1.4 | 22.0 ± 0.6 |
| Val | 14.1 ± 1.8 | 14.4 ± 0.4 |
| Met | 6.1 ± 0.4 | 5.8 ± 0.3 |
| Ile | 14.6 ± 1.7 | 10.3 ± 0.2 |
| Leu | 27.3 ± 2.1 | 27.8 ± 0.8 |
| Tyr | 10.7 ± 1.3 | 11.4 ± 0.4 |
| Phe | 11.6 ± 1.4 | 10.0 ± 0.2 |
| His | 14.1 ± 1.2 | 7.9 ± 0.6 |
| Trp | 4.4 ± 0.3 | 3.9 ± 0.4 |
| Lys | 11.9 ± 0.9 | 5.4 ± 0.2 |
| Arg | 13.9 ± 0.6 | 15.8 ± 0.4 |
| Cys** | 14.4 ± 0.2 | 14.2 ± 0.9 |
| Pro | 29.2 ± 0.9 | 29.6 ± 1.1 |

*Data corresponds to the mean ± SD of four analyses and normalized to a protein of 32,000 daltons.
**Cysteine was determined as cysteic acid after performic acid oxidation.

The inhibin Protein B from the final RP-HPLC purification was analyzed under reducing and non-reducing conditions in 1-mm-thick 15% acrylamide gel according to the method of Laemmli, V., *Nature* 227 68014 685 (1970). The protein was revealed by silver staining reagent (BIO-RAD, Richmond, Calif.). The following molecular weight standards were used to calibrate the gel: bovine serum albumin ($M_r$=67,000), ovalbumin ($M_r$=43,000), alpha-chymotrypsinogen ($M_r$=25,700) and lysozyme ($M_r$=14,500). In non-reducing condition, 2 μg of inhibin protein in 20 μl water was incubated with 20 μl sample buffer (0.152M Tris-HCl, pH 6.8, containing 20% glycerol (V/V), 4% sodium dodecylsulfate and 0.04% bromphenol blue) for 1 hour at 37° C. prior to loading onto the gel. The electrophoresis was performed at a constant 200 volts for 6 hours at room temperature. In reducing condition, 2 μg of protein was incubated, first with 20 μl of 0.02M dithiothreitol for 15 min at 37° C. and then 20 μl of sample buffer was added and the incubation continued for one more hour before the sample was applied to the gel. Electrophoresis was carried out as above, except that 0.005M dithiothreitol was included in the electrophoretic buffer. On SDS-PAGE under non-reducing condition, inhibin Protein B showed a single band migrating at $M_r$ 32,000 (See FIG. 3a). Under reducing condition, inhibin Protein B separated into two bands, one migrating at $M_r$ 18,000 and the other $M_r$ 14,000 (See FIG. 3b). Similar electrophoresis of Protein A showed two such bands plus one at $M_r$ 8,000 which was felt to possibly indicate the presence of impurity.

NH$_2$-terminal sequence analyses of the 18K and 14K chains of 32K inhibin Proteins A and B were accomplished by first separating the two chains by SDS-PAGE under reducing conditions, followed by electroblotting of the separated protein chains onto GF/C paper which was subsequently punched out for direct microsequencing. Briefly, each inhibin protein (12–15 μg) was electrophoresed on 0.5-mm-thick 15% acrylamide gel (8×10 cm) under reducing condition, as described above. After electrophoresis, the gel was immediately washed 3 times with 0.5% NP-40 (Sigma Chemical Co., St. Louis, Mo.) in 0.5% acetic acid at room temperature. The gel was then placed between 2 sheets of trifluoracetic acid-activated GF/C paper (Whatman, Clifton, N.J.) which had been wet briefly with the blotting buffer (2% acetic acid containing 0.5% NP-40). One more activated GF/C paper was placed on the cathode side in case the protein was not completely absorbed by the first paper. The outer surface of the GF/C paper was protected by Whatman No. 3 filter paper, and the whole assembly inserted between two Scotch-Brite pads held together by a plastic grid (BIO-RAD, Richmond, Calif.). This was electrophoresed in the blotting buffer at a constant voltage of 60 V for 16 hours at 4° C. to transfer the positively charged proteins onto the GF/C paper. The electrolytically transferred protein chains were revealed with Coomassie blue staining. 1.2 cm diameter circles were punched out of the stained protein bands and subjected directly to microsequencing as described above.

Microsequencing, as described in Esch, F. *Anal. Biochem.* 136, 39–47, 1984, of intact inhibin protein beginning at the NH$_2$-terminus had consistently revealed two residues of approximately equal concentration at every cycle, indicating each protein is composed of two chains. Based upon the results from multiple sequencing analyses of both intact and reduced inhibin proteins, the NH$_2$-terminal residues of the 18K chain of each inhibin protein are Ser-Thr-Ala-Pro-Leu-Pro-Trp-Pro-Trp- Ser-Pro-Ala-Ala-Leu-Arg-Leu-Leu-Gln-Arg-Pro-Pro-Glu-Glu-Pro-Ala-Val. The NH₂-terminal residues of the 14K chain of inhibin Protein B are Gly-Leu-Glu-Cys-Asp-Gly-Arg-Thr-Asn-Leu-Cys-Cys-Arg-Gln-Gln-Phe-Phe-Ile-Asp-Phe-Arg-Leu-Ile-Gly-Trp-, and the NH₂-terminal residues of the 14K chain of inhibin Protein A are Gly-Leu-Glu-Cys-Asp-Gly-Lys-Val-Asn-Ile-Cys-Cys-Lys-Lys-Gln-Phe-Phe-Val-Ser-Phe-Lys-Asp-Ile-Gly-Trp-Asn-Asp-Trp-Ile-Ile-Ala-Pro-.

Once a substantial portion of the sequence of the three chains of inhibin protein are known, the mRNA encoding the chains can be isolated, and the cDNA's can be synthesized by recombinant DNA techniques. Messenger RNA (mRNA) is obtained from ovarian follicules which produce inhibin, and then cDNA is synthesized from the mRNA by reverse transcription. The cDNA is inserted into a cloning vector which is used to transform a suitable host to create a cDNA library.

Based upon the known partial amino acid residue sequences of the three inhibin chains, labelled oligonucleotides are synthesized for detecting cDNA corresponding to each chain. Because of the degeneracy of the genetic code, mixed hybridization probes are prepared and used as probes. These probes are then used to select, from the library, cDNA clones that contain gene sequences encoding the chains. cDNA libraries may also be screened by immunological expression assay with antibody raised against inhibin or one of the inhibin chains. Immunological expression assay may also be used to confirm screening with hybridization probes.

From selected clones, cDNA is excised and inserted into appropriate vectors under the control of promotor sequences, and the vectors are transformed into cell lines for expression of the recombinant inhibin chains. Although vectors containing the genes for an appropriate pair of chains could conceivably be transformed into the same cell line, for simplicity, vectors for expression of each chain are preferably transformed separately into cell lines. The individual inhibin chains can then be isolated from the cellular material and/or the cell culture medium and are useful as intermediates for the preparation of the bioactive inhibin. Appropriate quantities of the 18K and the 14K chains are then subjected to oxidizing conditions which promote disulfide bonding between the chains to produce inhibin.

The foregoing molecular biology techniques may also be used to read the gene sequences encoding the separate inhibin chains, and thereby completely characterize the protein chains. Protein A has now been completely characterized and found to include a 134-residue chain (the 18K chain) that is linked by one or more disulfide bridges to a 116-residue chain (the 14K chain). The 134-residue chain has the following formula: H-Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val-His-Ala-Asp-Cys-His-Arg-Ala-Ser-Leu-Asn-Ile-Ser-Phe-Gln-Glu-Leu-Gly-Trp-Asp-Arg-Trp-Ile-Val-His-Pro-Pro-Ser-Phe-Ile-Phe-His-Tyr-Cys-His-Gly-Gly-C s-Gly-Leu-Pro-Thr-Leu-Pro-Asn-Leu-Pro-Leu-Ser-Val-Pro-Gly-Ala-Pro-Pro-Thr-Pro-Val-Gln-Pro-Leu-Leu-Leu-Val-Pro-Gly-Ala-Gln-Pro-Cys-Cys-Ala-Ala-Leu-Pro-Gly-Thr-Met-Arg-Ser-Leu-Arg-Val-Arg-Thr-Thr-Ser-Asp-Gly-Gly-Tyr-Ser-Phe-Lys-Tyr-Glu-Thr-Val-Pro-Asn- eu-Leu-Thr-Gln-His-Cys-Ala-Cys-Ile-OH. The 116-residue chain has the following formula: H-Gly-Leu-Glu-Cys-Asp-Gly-Lys-Val-Asn-Ile-Cys-Cys-Lys-Lys-Gln-Phe-Phe-Val-Ser-Phe-Lys-Asp-Ile-Gly-Trp-Asn-Asp-Trp-Ile-Ile-Ala-Pro-Ser-Gly-Tyr-His-Ala-Asn-Tyr-Cys-Glu-Gly-Glu-Cys-Pro-Ser-His-Ile-Ala-Gly-Thr-Ser-Gly-Ser-Ser-Leu-Ser-Phe-His-Ser-Thr-Val- le-Asn-His-Tyr-Arg-Met-Arg-Gly-His-Ser-Pro-Phe-Ala-Asn-Leu-Lys-Ser-Cys-Cys-Val-Pro-Thr-Lys-Leu-Arg-Pro-Met-Ser-Met-Leu-Tyr-Tyr-Asp-Asp-Gly-Gln-Asn-Ile-Ile-Lys-Lys-Asp-Ile-Gln-Asn-Met-Ile-Val-Glu-Glu-Cys-Gly-Cys-Ser-OH.

This characterization is in agreement with the earlier analyses of the purified protein material obtained from PFF; the disparity between the number of residues in the first chain and the measured value of 18K is accounted for by the presence of the aforementioned glycosylation. It is believed that a carbohydrate moiety having a molecular weight of about 3000 daltons is attached to the side chain of the Asn residue in the 36-position of the first chain.

Protein B has also been characterized and the 18K chain is believed to have the same sequence as Protein A. The 14K chain has been found to have the following 115-residue formula: H-Gly-Leu-Glu-Cys-Asp-Gly-Arg-Thr-Asn-Leu-Cys-Cys-Arg-Gln-Gln-Phe-Phe-Ile-Asp-Phe- Arg-Leu-Ile-Gly-Trp-Ser-Asp-Trp-Ile-Ile-Ala-Pro-Thr-Gly-Tyr-Tyr-Gly-Asn-Tyr-Cys-Glu-Gly-Ser-Cys-Pro-Ala-Tyr-Leu-Ala-Gly-Val-Pro-Gly-Ser-Ala-Ser-Ser-Phe-His-Thr-Ala-Val-Val-Asn-Gln-Tyr-Arg-Met-Arg-Gly-Leu-Asn-Pro-Gly-Thr-Val-Asn-Ser-Cys-Cys-Ile-Pro-Th -Lys-Leu-Ser-Thr-Met-Ser-Met-Leu-Tyr-Phe-Asp-Asp-Glu-Tyr-Asn-Ile-Val-Lys-Arg-Asp-Val-Pro-Asn-Met-Ile-Val-Glu-Glu-Cys-Gly-Cys-Ala-OH. This characterization is in agreement with the earlier analyses of the purified protein material obtained from PFF.

Substantially pure 32K inhibin or the nontoxic salts thereof, combined with a pharmaceutically acceptable carrier to form a pharmaceutical composition, may be administered to mammals, including humans, either intravenously, subcutaneously, percutaneously, intramuscularly or orally for control of fertility. Administration of inhibin induces decreased fertility in female mammals and decreases spermatogenesis in male mammals. Administration of a sufficient amount of inhibin induces infertility in mammals. Inhibin is also useful for tests to diagnose infertility.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

Inhibin should be administered under the guidance of a physician, and pharmaceutical compositions will usually contain an effective amount of the peptide in conjunction with a conventional, pharmaceutically-acceptable carrier. The dosage will vary depending upon the specific purpose for which the protein is being administered, and dosage levels in the range of about 0.1 to about 1 milligrams per Kg. of body weight may be used when the protein is administered on a regular basis as a male contraceptive.

Although the method of purification of inhibin has been described primarily in terms of isolation from PFF, inhibin can be similarly purified from other crude extracts. The term "crude extracts" as used herein refers to other mammalian body material in addition to follicular fluid, as well as to extracts from organisms including laboratory microorganisms such as prokaryotes and eukaryotes which have been transformed by means of state of the art methodology to manufacture mammalian inhibin protein.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

Particular features of the invention are emphasized in the claims which follow.

What is claimed:

1. A 32,000-dalton protein having a purity of at least about 90% by weight of total proteins, said protein having a pKa of about 4.8, said protein being composed of a first polypeptide chain having a molecular weight of about 18,000 and a second polypeptide chain having a molecular weight of about 14,000 daltons, said first chain and said second chain being linked to each other through disulfide bonding in the active protein, said first chain having an amino-terminal sequence beginning with Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val and said second chain having an amino-terminal sequence beginning with Gly-Leu-Glu-Cys-Asp-Gly, said protein specifically inhibiting basal secretion of follicle-stimulating hormone while not inhibiting basal secretion of luteinizing hormone.

2. A protein according to claim 1 wherein said second chain has an amino terminal sequence beginning with Gly-Leu-Glu-Cys-Asp-Gly-Arg-Thr-Asn-Leu.

3. A protein according to claim 1 wherein said second chain has an amino terminal sequence beginning with Gly-Leu-Glu-Cys-Asp-Gly-Arg-Thr-Asn-Leu-X-Cys-Arg-Gln-Gln-Phe-Phe-Ile-Asp-Phe-Arg-Leu-Ile-Gly-Trp, wherein X is an unknown amino acid residue.

4. A protein according to claim 1 wherein said second chain has the amino-terminal sequence: H-Gly-Leu-Glu-cys-Asp-Gly-Lys-Val-Asn-Ile-Cys-Cys-Lys-Lys-Gln-Phe-Phe-Val-Ser-Phe-Lys-Asp-Ile-Gly-Trp-Asn-Asp-Trp-Ile-Ile-Ala-Pro.

5. A protein according to claim 1 wherein said second chain has the formula: H-Gly-Leu-Glu-Cys-Asp-Gly-Lys-Val-Asn-Ile-Cys-Cys-Lys-Lys-Gln-Phe-Phe-Val-Ser-Phe-Lys-Asp-Ile-Gly-Trp-Asn-Asp-Trp-Ile-Ile-Ala-Pro-Ser-Gly-Tyr-His-Ala-Asn-Tyr-Cys-Glu-Gly-Glu-Cys-Pro-Ser-His-Ile-Ala-Gly-Thr-Ser-Gly-Ser-Ser-Leu-Ser-Phe-His-Ser-Thr-Val- le-Asn-His-Tyr-Arg-Met-Arg-Gly-His-Ser-Pro-Phe-Ala-Asn-Leu-Lys-Ser-Cys-Cys-Val-Pro-Thr-Lys-Leu-Arg-Pro-Met-Ser-Met-Leu-Tyr-Tyr-Asp-Asp-Gly-Gln-Asn-Ile-Ile-Lys-Lys-Asp-Ile-Gln-Asn-Met-Ile-Val-Glu-Glu-Cys-Gly-Cys-Ser-OH.

6. A protein according to claim 1 having an amino acid composition of about Asx 21.0, Thr 13.5. Ser 18.1, Glx 22.5, Gly 22.4, Ala 22.0, Val 14.4, Met 5.8, Ile 10.3, Leu 27.8, Tyr 11.4, Phe 10.0, His 7.9, Trp 3.9, Lys 5.4, Arg 15.8, Cys 14.2, and Pro 29.6.

7. A protein according to claim 1 having an amino acid composition of about Asx 18.5, Thr 11.5. Ser 16.3, Glx 21.3, Gly 19.9, Ala 19.7, Val 14.1, Met 6.1, Ile 14.6, Leu 27.3, Tyr 10.7, Phe 11.6, His 14.1, Trp 4.4, Lys 11.9, Arg 13.9, Cys 14.4, and Pro 29.2.

8. A protein according to claim 1 wherein said first chain has the formula: H-Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val-His-Ala-Asp-Cys-His-Arg-Ala-Ser-Leu-Asn-Ile-Ser-Phe-Gln-Glu-Leu-Gly-Trp-Asp-Arg-Trp-Ile-Val-His-Pro-Pro-Ser-Phe-Ile-Phe-His-Tyr-Cys-His-Gly-Gly- ys-Gly-Leu-Pro-Thr-Leu-Pro-Asn-Leu-Pro-Leu-Ser-Val-Pro-Gly-Ala-Pro-Pro-Thr-Pro-Val-Gln-Pro-Leu-Leu-Leu-Val-Pro-Gly-Ala-Gln-Pro-Cys-Cys-Ala-Ala-Leu-Pro-Gly-Thr-Met-Arg-Ser-Leu-Arg-Val-Arg-Thr-Thr-Ser-Asp-Gly-Gly-Tyr-Ser-Phe-Lys-Tyr-Glu-Thr-Val-Pro-Asn- eu-Leu-Thr-Gln-His-Cys-Ala-Cys-Ile-OH and is glycosylated.

9. A protein according to claim 5 wherein said first chain has the formula: H-Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val-His-Ala-Asp-Cys-His-Arg-Ala-Ser-Leu-Asn-Ile-Ser-Phe-Gln-Glu-Leu-Gly-Trp-Asp-Arg-Trp-Ile-Val-His-Pro-Pro-Ser-Phe-Ile-Phe-His-Tyr-Cys-His-Gly-Gly- ys-Gly-Leu-Pro-Thr-Leu-Pro-Asn-Leu-Pro-Leu-Ser-Val-Pro-Gly-Ala-Pro-Pro-Thr-Pro-Val-Gln-Pro-Leu-Leu-Leu-Val-Pro-Gly-Ala-Gln-Pro-Cys-Cys-Ala-Ala-Leu-Pro-Gly-Thr-Met-Arg-Ser-Leu-Arg-Val-Arg-Thr-Thr-Ser-Asp-Gly-Gly-Tyr-Ser-Phe-Lys-Tyr-Glu-Thr-Val-Pro-Asn- eu-Leu-Thr-Gln-His-Cys-Ala-Cys-Ile-OH.

10. A protein according to claim 1 wherein said second chain has the formula: H-Gly-Leu-Glu-Cys-Asp-Gly-Arg-Thr-Asn-Leu-Cys-Cys-Arg-Gln-Gln-Phe-Phe-Ile-Asp-Phe-Arg-Leu-Ile-Gly-Trp-Ser-Asp-Trp-Ile-Ile-Ala-Pro-Thr-Gly-Tyr-Tyr-Gly-Asn-Tyr-Cys-Glu-Gly-Ser-Cys-Pro-Ala-Tyr-Leu-Ala-Gly-Val-Pro-Gly-Ser-Ala-Ser-Ser-Phe-His-Thr-Ala-Val- al-Asn-Gln-Tyr-Arg-Met-Arg-Gly-Leu-Asn-Pro-Gly-Thr-Val-Asn-Ser-Cys-Cys-Ile-Pro-Thr-Lys-Leu-Ser-Thr-Met-Ser-Met-Leu-Tyr-Phe-Asp-Asp-Glu-Tyr-Asn-Ile-Val-Lys-Arg-Asp-Val-Pro-Asn-Met-Ile-Val-Glu-Glu-Cys-Gly-Cys-Ala-OH 11. A protein according to claim 10 wherein said first chain has the formula: H-Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val-His-Ala-Asp-Cys-His-Arg-Ala-Ser-Leu-Asn-Ile-Ser-Phe-Gln-Glu-Leu-Gly-Trp-Asp-Arg-Trp-Ile-Val-His-Pro-Pro-Ser-Phe-Ile-Phe-His-Tyr-Cys-His-Gly-Gly- ys-Gly-Leu-Pro-Thr-Leu-Pro-Asn-Leu-Pro-Leu-Ser-Val-Pro-Gly-Ala-Pro-Pro-Thr-Pro-Val-Gln-Pro-Leu-Leu-Leu-Val-Pro-Gly-Ala-Gln-Pro-Cys-Cys-Ala-Ala-Leu-Pro-Gly-Thr-Met-Arg-Ser-Leu-Arg-Val-Arg-Thr-Thr-Ser-Asp-Gly-Gly-Tyr-Ser-Phe-Lys-Tyr-Glu-Thr-Val-Pro-Asn- eu-Leu-Thr-Gln-His-Cys-Ala-Cys-Ile-OH.

12. A method of obtaining substantially homogeneous proteins having inhibin activity from crude extracts comprising procuring extract material having inhibin activity,
exposing said extract to a support medium to which heparin moieties are attached under such conditions that inhibin proteins adsorb to said heparin moieties, and subsequently eluting said inhibin proteins from said heparin moieties, gel filtrating said eluted inhibin proteins and selecting fractions having inhibin activity, and fractionating said gel filtrated fractions on at least one reverse-phase high performance liquid chromatography column.

13. A method according to claim 12 wherein said gel filtrated fractions are fractionated on at least two successive reverse-phase high performance liquid chromatography columns of different solid and/or liquid phase conditions.

14. A method according to claim 12 wherein said gel filtrated fractions are fractionated on at least four successive reverse-phase high performance liquid chromatography columns of different solid and/or liquid phase conditions.

15. A method according to claim 12 wherein said RP-HPLC is performed on a C3–C5 column.

16. A method according to claim 12 wherein the liquid phase in said RP-HPLC is a gradient of acetonitrile.

17. A method according to claim 12 wherein said crude extract is obtained from porcine body material.

18. A method according to claim 17 wherein said body material is porcine follicular fluid.

19. A synthetic protein produced by recombinant DNA techniques or the like having two chains interconnected by disulfide bonding, said first chain having formula: H-Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val-His-Ala-Asp-Cys-His-Arg-Ala-Ser-Leu-Asn-Ile-Ser-Phe-Gln-Glu-Leu-Gly-Trp-Asp-Arg-Trp-Ile-Val-His-Pro-Pro-Ser-Phe-Ile-Phe-His-Tyr-Cys-His-Gly-Gly-Cys-Gly-Leu-Pro-Thr-Leu-Pro-Asn-Leu-Pr -Leu-Ser-Val-Pro-Gly-Ala-Pro-Pro-Thr-Pro-Val-Gln-Pro-Leu-Leu-Leu-Val-Pro-Gly-Ala-Gln-Pro-Cys-Cys-Ala-Ala-Leu-Pro-Gly-Thr-Met-Arg-Ser-Leu-Arg-Val-Arg-Thr-Thr-Ser-Asp-Gly-Gly-Tyr-Ser-Phe-Lys-Tyr-Glu-Thr-Val-Pro-Asn-Leu-Leu-Thr-Gln-His-Cys-Ala-Cys-Ile-OH and said second chain having either the formula: H-Gly-Leu-Glu-Cys-Asp-Gly-Lys-Val-Asn-Ile-Cys-Cys-Lys-Lys-Gln-Phe-Phe-Val-Ser-Phe-Lys-Asp-Ile-Gly-Trp-Asn-Asp-Trp-Ile-Ile-Ala-Pro-Ser-Gly-Tyr-His-Ala-Asn-Tyr-Cys-Glu-Gly-Glu-Cys-Pro-Ser-His-Ile-Ala-Gly-Thr-Ser-Gly-Ser-Ser-Leu-Ser-Phe-His-Ser-Thr-Val- le-Asn-His-Tyr-Arg-Met-Arg-Gly-His-Ser-Pro-Phe-Ala-Asn-Leu-Lys-Ser-Cys-Cys-Val-Pro-Thr-Lys-Leu-Arg-Pro-Met-Ser-Met-Leu-Tyr-Tyr-Asp-Asp-Gly-Gln-Asn-Ile-Ile-Lys-Lys- Asp-Ile-Gln-Asn-Met-Ile-Val-Glu-Glu-Cys-Gly-Cys-Ser-OH, or the formula H-Gly-Leu-Glu-Cys-Asp-Gly-Arg-Thr-Asn-Leu-Cys-Cys-Arg-Gln-Gln-Phe-Phe-Ile-Asp-Phe-Arg-Leu-Ile-Gly-Trp-Ser-Asp-Trp-Ile-Ile-Ala-Pro-Thr-Gly-Tyr-Tyr-Gly-Asn-Tyr-Cys-Glu-Gly-Ser-Cys-Pro-Ala-Tyr-Leu-Ala-Gly-Val-Pro-Gly-Ser-Ala-Ser-Ser-Phe-His-Thr-Ala-Val- al-Asn-Gln-Tyr-Arg-Met-Arg-Gly-Leu-Asn-Pro-Gly-Thr-Val-Asn-Ser-Cys-Cys-Ile-Pro-Thr-Lys-Leu-Ser-Thr-Met-Ser-Met-Leu-Tyr-Phe-Asp-Asp-Glu-Tyr-Asn-Ile-Val-Lys-Arg-Asp-Val-Pro-Asn-Met-Ile-Val-Glu-Glu-Cys-Gly-Cys-Ala-OH.

20. A synthetic protein useful for the production of synthetic inhibin, which protein is selected from the group consisting of: (a) H-Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val-His-Ala-Asp-Cys-His-Arg-Ala-Ser-Leu-Asn-Ile-Ser-Phe-Gln-Glu-Leu-Gly-Trp-Asp-Arg-Trp-Ile-Val-His-Pro-Pro-Ser-Phe-Ile-Phe-His-Tyr-Cys-His-Gly-Gly- ys-Gly-Leu-Pro-Thr-Leu-Pro-Asn-Leu-Pro-Leu-Ser-Val-Pro-Gly-Ala-Pro-Pro-Thr-Pro-Val-Gln-Pro-Leu-Leu-Leu-Val-Pro-Gly-Ala-Gln-Pro-Cys-Cys-Ala-Ala-Leu-Pro-Gly-Thr-Met-Arg-Ser-Leu-Arg-Val-Arg-Thr-Thr-Ser-Asp-Gly-Gly-Tyr-Ser-Phe-Lys-Tyr-Glu-Thr-Val-Pro-Asn- eu-Leu-Thr-Gln-His-Cys-Ala-Cys-Ile-OH; (b) H-Gly-Leu-Glu-Cys-Asp-Gly-Arg-Thr-Asn-Leu-Cys-Cys-Arg-Gln-Gln-Phe-Phe-Ile-Asp-Phe-Arg-Leu-Ile-Gly-Trp-Ser-Asp-Trp-Ile-Ile-Ala-Pro-Thr-Gly-Tyr-Tyr-Gly-Asn-Tyr-Cys-Glu-Gly-Ser-Cys-Pro-Ala-Tyr-Leu-Ala-Gly-Val-Pro-Gly-Ser-Ala-Ser-Ser-Phe-His-Thr-Ala-Val- al-Asn-Gln-Tyr-Arg-Met-Arg-Gly-Leu-Asn-Pro-Gly-Thr-Val-Asn-Ser-Cys-Cys-Ile-Pro-Thr-Lys-Leu-Ser-Thr-Met-Ser-Met-Leu-Tyr-Phe-Asp-Asp-Glu-Tyr- sn-Ile-Val-Lys-Arg-Asp-Val-Pro-Asn-Met-Ile-Val-Glu-Glu-Cys-Gly-Cys-Ala-OH and (c) H-Gly-Leu-Glu-Cys-Asp-Gly-Lys-Val-Asn-Ile-Cys-Cys-Lys-Lys-Gln-Phe-Phe-Val-Ser-Phe-Lys-Asp-Ile-Gly-Trp-Asn-Asp-Trp-Ile-Ile-Ala-Pro-Ser-Gly-Tyr-His-Ala-Asn-Tyr-Cys-Glu-Gly-Glu-Cys-Pro-Ser-His-Ile-Ala-Gly-Thr-Ser-Gly-Ser-Ser-Leu-Ser-Phe-His-Ser-Thr-Val-I e-Asn-His-Tyr-Arg-Met-Arg-Gly-His-Ser-Pro-Phe-Ala-Asn-Leu-Lys-Ser-Cys-Cys-Val-Pro-Thr-Lys-Leu-Arg-Pro-Met-Ser-Met-Leu-Tyr-Tyr-Asp-Asp-Gly-Gln-Asn-Ile-Ile-Lys-Lys-Asp-Ile-Gln-Asn-Met-Ile-Val-Glu-Glu-Cys-Gly-Cys-Ser-OH.

* * * * *

UNITED STATES PATENT AND TRADEMARK OFFICE
CERTIFICATE OF CORRECTION

PATENT NO. : 4,740,587

DATED : April 26, 1988

INVENTOR(S) : Nicholas C. Ling et al.

Page 1 of 2

It is certified that error appears in the above-identified patent and that said Letters Patent is hereby corrected as shown below:

On The Title Page:

ABSTRACT, Line 6, Change "molecular" to --molecule--,

ABSTRACT, Line 28, Change "does" to --dose--.

Column 1, Line 6, Change "Institute" to --Institutes--.

Column 6, Line 44, Change "a" to --as--.

Column 9, Line 60, Change "C s" to --Cys--.

Column 9, Line 65, Change " eu" to --Leu--.

Column 10, Line 4, Change " le" to --Ile--.

Column 10, Line 28, Change "Th " to --Thr--.

Column 11, Line 60, Change " le" to --Ile--.

Column 12, Line 14, Change "ys" to --Cys--.

Column 12, Line 19, Change "eu" to --Leu--.

Column 12, Line 28, Change "ys" to --Cys--.

Column 12, Line 33, Change "eu" to --Leu--.

Column 12, Line 41, Change " al" to --Val--.

Column 12, Line 53, Change " ys" to --Cys--.

Column 12, Line 58, Change "eu" to --Leu--.

Column 13, Line 34, Change "Pr" to --Pro--.

Column 13, Line 45, Change " le" to --Ile--.

Column 14, Line 7, Change " al" to --Val--,

Column 14, Line 20, Change "ys" to --Cys--.

Column 14, Line 25, Change "eu" to --Leu--,

UNITED STATES PATENT AND TRADEMARK OFFICE
CERTIFICATE OF CORRECTION

PATENT NO. : 4,740,587

DATED : April 26, 1988

INVENTOR(S) : Nicholas C. Ling et al.

It is certified that error appears in the above-identified patent and that said Letters Patent is hereby corrected as shown below:

Column 14, Line 33, Change "al" to --Val--,

Column 14, Line 36, Change "sn" to --Asn--,

Column 14, Lines 42-43, Change "Ie" to --Ile--.

Signed and Sealed this

First Day of November, 1988

Attest:

DONALD J. QUIGG

Attesting Officer

Commissioner of Patents and Trademarks